US 6,652,140 B1

United States Patent
Taber et al.

(10) Patent No.: US 6,652,140 B1
(45) Date of Patent: Nov. 25, 2003

(54) X-RAY CASSETTE HOLDER APPARATUS

(75) Inventors: Tanya Taber, Lawrenceburg, IN (US); Craig A. Coder, Redmond, WA (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 09/528,571

(22) Filed: Mar. 20, 2000

Related U.S. Application Data
(60) Provisional application No. 60/125,375, filed on Mar. 19, 1999.

(51) Int. Cl.[7] ................................................ G03B 42/02
(52) U.S. Cl. ..................... 378/177; 378/188; 378/208; 378/209; 378/180
(58) Field of Search ................................. 378/177, 181, 378/208, 209, 180

(56) References Cited

U.S. PATENT DOCUMENTS

| | | | |
|---|---|---|---|
| 1,768,769 A | | 7/1930 | Kelley |
| 3,694,653 A | * | 9/1972 | Allard et al. ............... 248/476 |
| 3,774,045 A | | 11/1973 | Trott |
| 3,795,815 A | | 3/1974 | Weinstock et al. |
| 3,968,374 A | | 7/1976 | Schroeder |
| 4,156,145 A | * | 5/1979 | Weatherholt ................ 378/177 |
| 4,193,148 A | | 3/1980 | Rush |
| 4,464,780 A | | 8/1984 | Ruiz |
| 4,553,786 A | * | 11/1985 | Lockett, et al. .......... 297/440.1 |
| 4,584,989 A | | 4/1986 | Stith |
| 4,651,364 A | | 3/1987 | Hayton et al. |
| 4,893,323 A | * | 1/1990 | Cook, III .................... 378/177 |
| 4,916,725 A | | 4/1990 | Quinter et al. |
| 4,926,457 A | | 5/1990 | Poehner et al. |
| 5,016,268 A | | 5/1991 | Lotman |
| 5,138,646 A | | 8/1992 | Hubert et al. |
| 5,255,303 A | | 10/1993 | DiMaio et al. |
| 5,422,928 A | | 6/1995 | Payne |
| 5,575,026 A | | 11/1996 | Way et al. ..................... 5/617 |
| 5,703,925 A | | 12/1997 | Wright |
| 5,996,149 A | | 12/1999 | Heimbrock et al. |

FOREIGN PATENT DOCUMENTS

| | | | |
|---|---|---|---|
| DE | 43 44 123 A1 | 6/1995 | |
| FR | 2534707 | 4/1984 | |
| GB | 1 200 814 | 8/1970 | |
| JP | 02001029401 | * 2/2001 | ............ A61G/7/10 |
| WO | WO99/15126 | 4/1999 | |

OTHER PUBLICATIONS

"Advantage Series Trauma Stretcher Model 1002," Stryker Patient Handling brochure, three pages, Sep. 1993.

"Full Length X–Ray Trauma Stretcher Model 1020 renaissance Series," Stryker Medical brochure, two pages, May 1995.

"530 ED/Trauma Stretcher," Midmark Corporation brochure, six pages, 1989.

(List continued on next page.)

Primary Examiner—David V. Bruce
Assistant Examiner—Courtney Thomas
(74) Attorney, Agent, or Firm—Bose McKinney & Evans LLP (57) ABSTRACT

An apparatus to couple rigid items to a patient support including a patient support coupler and a holder.

67 Claims, 5 Drawing Sheets

OTHER PUBLICATIONS

"The Midmark 550/555 Stretcher," Midmark Corporation brochure, four pages, 1995.

"ED II Emergency Department Stretcher," Stryker Medical Division product brochure, two pages, published at least as early as Feb. 2, 1998.

"921 InstaCare Trauma/Emergency Stretcher Modifications," Stryker Medical brochure, two pages, published at least as early as Feb. 2, 1998.

"Beta One X–Ray Bed," Beta Medical Products, Inc. brochure, two pages, published at least as early as Feb. 2, 1998.

"X–Ray Trauma Stretcher," Beta Medical Products, Inc. brochure, two pages, published at least as early as Feb. 2, 1998.

"Patient Handling Systems," Stryker Medical Division brochure, two pages, published at least as early as Feb. 2, 1998.

"InstaCare/Emergency Stretcher Model 1000E," Stryker Medical brochure, two pages, published at least as early as Feb. 2, 1998.

"The Gemini Series," Hausted brochure, two pages, published at least as early as Feb. 2, 1998.

"Hausted Specialty Stretchers. The Unicare Series" Hausted product brochure, two pages, published at least as early as Feb. 2, 1998.

"Colson Trauma Stretcher," Colson brochure, one page published at least as early as Feb. 2, 1998.

"Here are just a few of the ways a C–100 cassette holder from Monec X–Ray Works can help you!," Monec X–Ray Works brochure, four pages, published at least as early as Feb. 2, 1998.

"Dual Control Critical Care Bed Model 2020,"Stryker Medical brochure, two pages, published at least as early as Feb. 2, 1998.

* cited by examiner

Fig. 4 ial appli-
X-RAY CASSETTE HOLDER APPARATUS

This application claims benefit of U.S. provisional application Ser. No. 60/125,375 filed Mar. 19, 1999, the disclosure of which is expressly incorporated by reference herein.

BACKGROUND AND SUMMARY OF THE INVENTION

The present invention relates to hospital beds. More particularly, the present invention permits a patient to be x-rayed while positioned on the bed.

It is known to provide hospital beds having a support surface that is transparent to x-rays so that x-rays of a patient's upper body can be performed without removing the patient from the bed. See, for example, U.S. Pat. No. 5,996,149.

According to the present invention, an apparatus is provided to couple rigid items to a patient support. The apparatus includes a patient support coupler and a holder. The patient support coupler is adapted to couple to the patient support and is made of a material having a coefficient of friction. The holder is coupled to the patient support coupler and is configured to receive and hold a rigid item. The holder includes a surface having a coefficient of friction that is less than the coefficient of friction of the patient support coupler.

In addition, according to the present invention, an apparatus is provided to couple rigid items to a patient support. The apparatus includes a patient support coupler adapted to couple to the patient support and a holder coupled to the patient support coupler. The holder is configured to receive and hold a rigid item and is made of a pliable material.

Further, according to the present invention, an apparatus is provided to couple rigid items to a patient support that includes a support surface. The apparatus includes a patient support coupler adapted to couple to the patient support and a holder coupled to the patient support coupler. The holder is configured to receive and hold a rigid item and is positioned on an upper surface of the support surface.

Additional features of the disclosure will become apparent to those skilled in the art upon consideration of the following detailed description when taken in conjunction with the accompanying drawings.

DETAILED DESCRIPTION OF THE DRAWINGS

Figure 1:
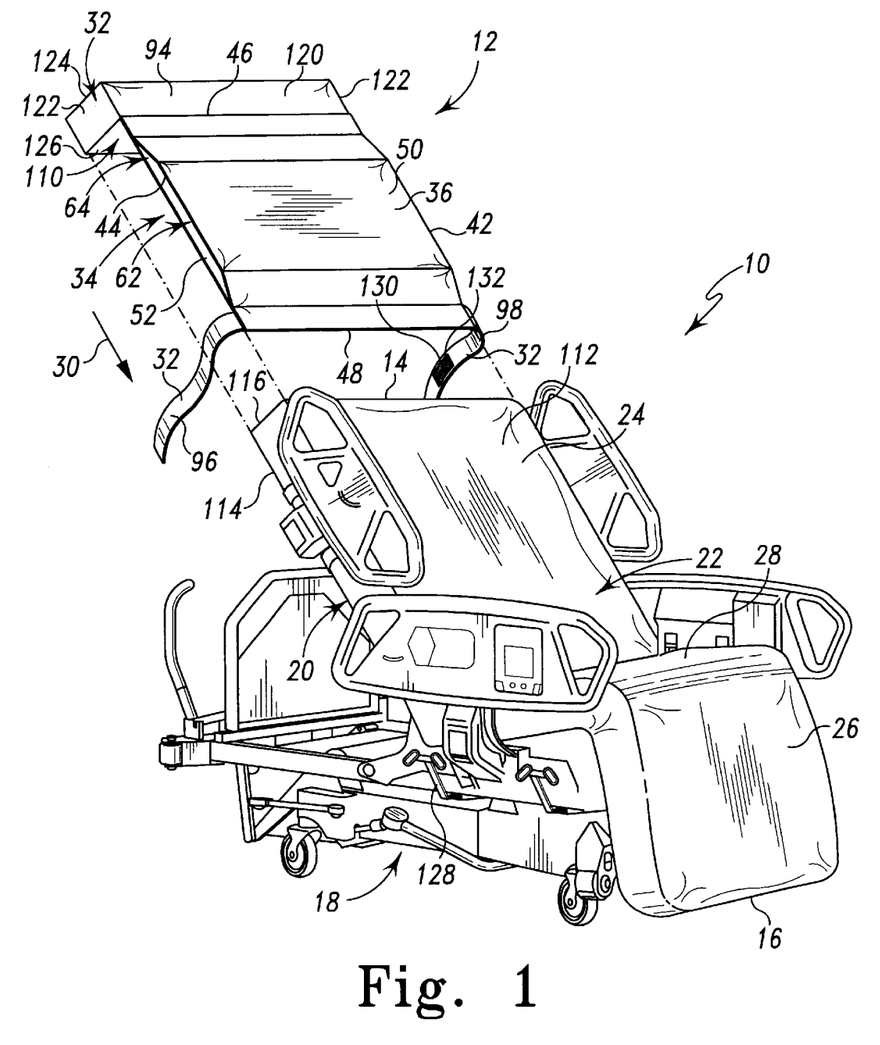
FIG. 1 is a perspective view of a hospital bed and an x-ray apparatus exploded away from the hospital bed.

A hospital bed or patient support 10 having an x-ray apparatus 12 is shown in FIG. 1. The hospital bed 10 includes a head end 14, a foot end 16, a frame 18, an articulating deck 20 movable relative to frame 18, and a mattress or patient support surface 22 positioned on deck 20. The x-ray apparatus 12 is coupled to head end 14 of bed 10 so that a rigid item such as an x-ray cassette or CPR board can be positioned between mattress 22 and a patient lying on mattress 22.

Figure 2:
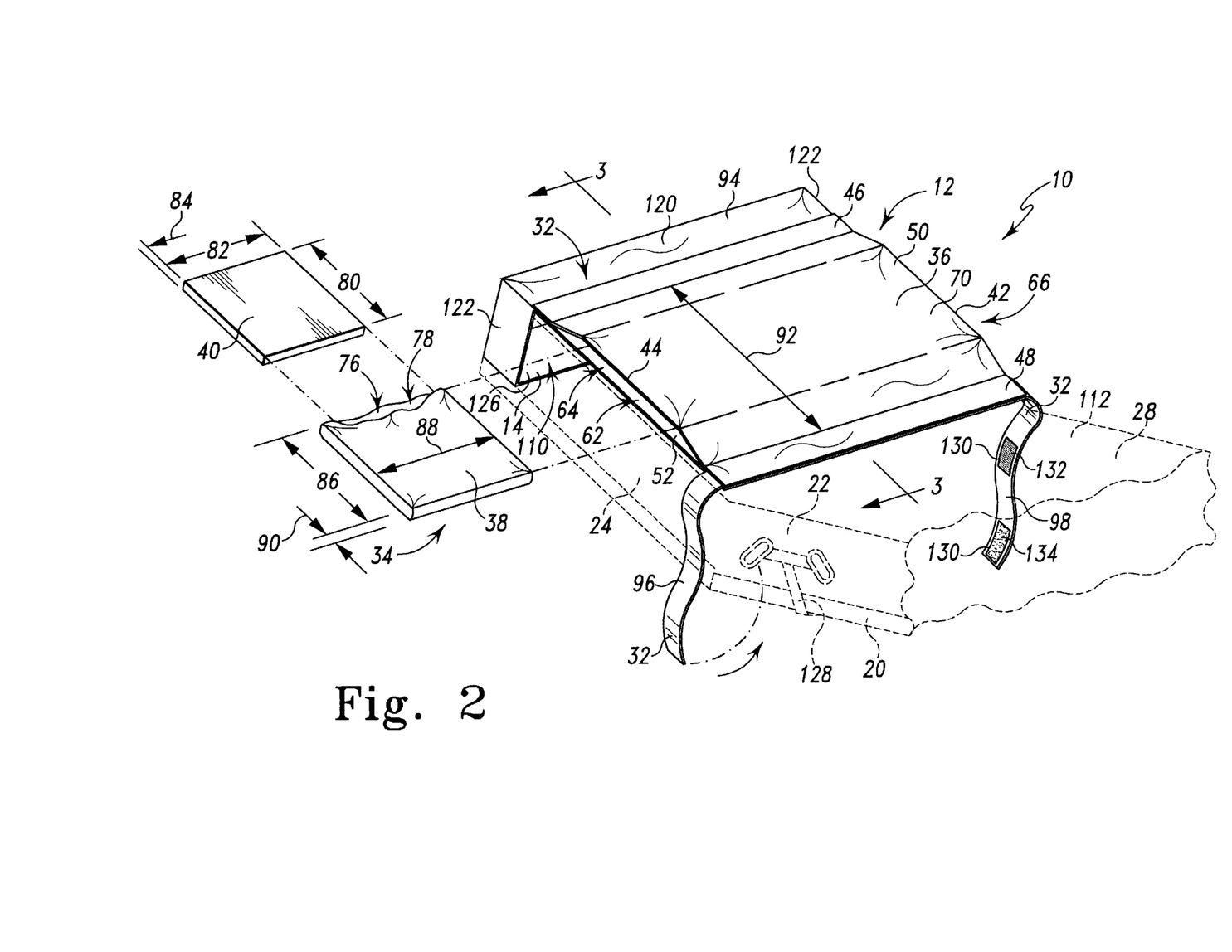
FIG. 2 is an exploded perspective view of the x-ray apparatus and a portion of the hospital bed showing the x-ray apparatus including a bed coupler and an x-ray cassette holder positioned on an upper surface of a mattress of the hospital bed and a separate receptacle adapted to receive and hold an x-ray cassette.
Figure 3:
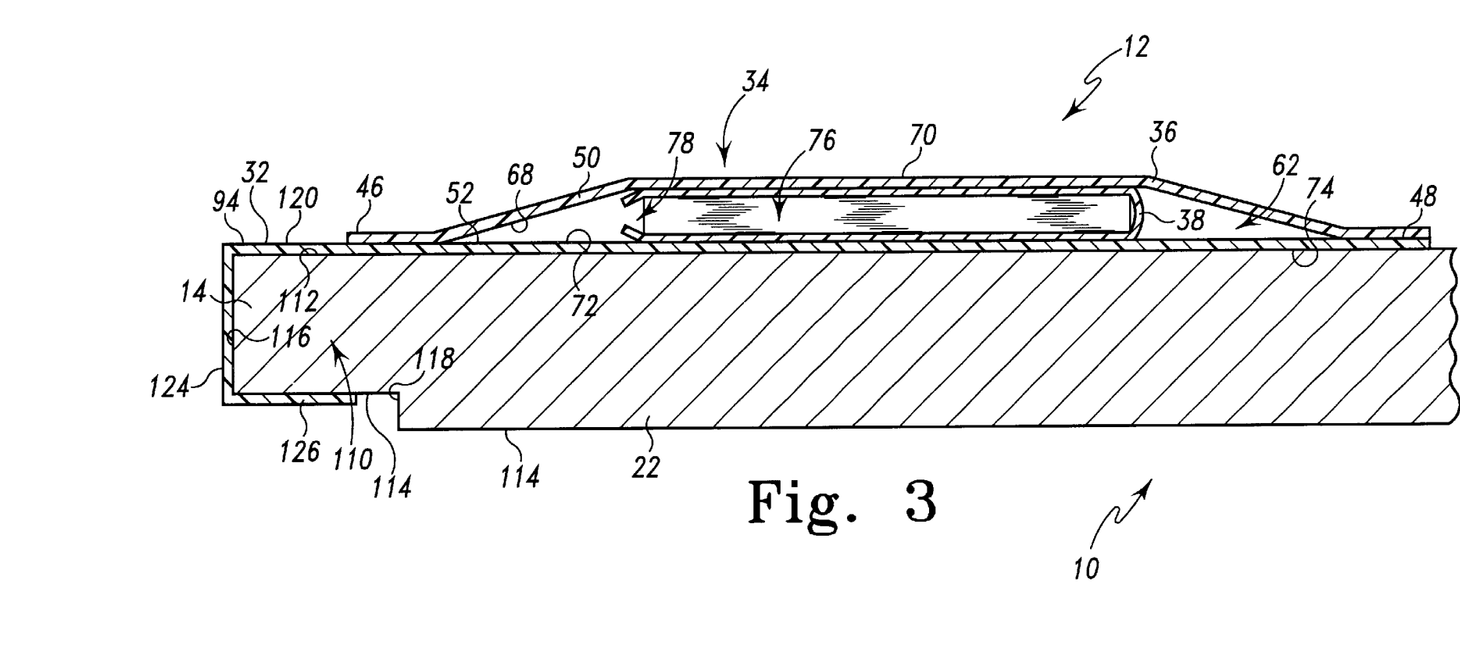
FIG. 3 is a sectional view taken along line 3—3 of FIG. 2 showing the x-ray cassette positioned in the x-ray cassette holder.

The mattress 20, shown in FIGS. 1–3, includes a head portion 24 at the head end 14 of the bed 10, a foot portion 26 at the foot end 16 of the bed 10, and a central portion 28 positioned between head and foot portions 24, 26. The x-ray apparatus 12 is coupled to head portion 24 of mattress 22 by sliding x-ray apparatus 12 in direction 30 onto head portion 24 of mattress 22. Preferably, the head portion 24 of mattress 22 is positioned upwardly at an angle relative to the central portion 28, as shown in FIG. 1, when the caregiver slides x-ray apparatus 12 onto mattress 22.

The x-ray apparatus 12 includes a patient support or bed coupler 32 and an item holder 34, as shown, for example, in FIGS. 1–3. The holder 34 includes first and second receptacles 36, 38 that receive and hold a rigid item such as an x-ray cassette 40. In the illustrated embodiment, the first receptacle 36 is a pouch having spaced-apart first and second sides 42, 44, spaced-apart first and second ends 46, 48 extending between the first and second sides 42, 44, and upper and lower layers 50, 52. The upper and lower layers 50, 52 are coupled at their first and second ends 46, 48 and at portions of their first and second sides 42, 44 adjacent to the ends 46, 48 to define a cavity 62. Openings 64, 66 in communication with cavity 68 are defined on first and second sides 42, 44 by the portions of upper and lower layers 50, 52 which are not coupled to each other. The upper layer 50 of first receptacle 36 includes a lower surface 68 facing into and defining cavity 62 and an upper surface 70 on which a patient lies when lying in bed 10 as shown in FIG. 3. The lower layer 52 of first receptacle 36 includes an upper surface 72 facing into and defining cavity 62 and a lower surface 74 facing toward and lying on mattress 22.

The second receptacle 38 includes a cavity 76 and an opening 78 into cavity 76 as shown in FIGS. 2 and 3. The x-ray cassette 40 is positioned in cavity 76 of second receptacle 38 by sliding the cassette 40 through the opening 78 into cavity 76. In the illustrated embodiment, the x-ray cassette 40 has a length 80 of 18⅛ inches, a width 82 of 15⅛ inches, and a thickness 84 of ½ inch. To facilitate insertion of x-ray cassette 40 into second receptacle 38, second receptacle 38 has an interior length 86 greater than 18⅛ inches, an interior width 88 greater than 15⅛ inches, and an interior height 90 greater than ½ inch.

Once the cassette 40 is positioned in second receptacle 38, the second receptacle 38 is slid through one of openings 64, 66 of the first receptacle 36 into cavity 62 of first receptacle 36. To facilitate placement of x-ray cassette 40 relative to a patient positioned on bed 10 to obtain a desired x-ray image, openings 64, 66 along sides 42, 44 of the first receptacle 36 have a length 92 that is substantially greater than length 86 of second receptacle 38.

The bed coupler 32 of x-ray apparatus 12 includes a receptacle 94 coupled to first end 46 of first receptacle 36 of holder 34 and first and second straps 96, 98 coupled to second end 48 of first receptacle 36 of holder 34. The receptacle 94 defines a cavity 110 in which a section of head portion 24 of mattress 22 is positioned as shown in FIGS. 2 and 3. In the illustrated embodiment shown in FIGS. 1–3, the mattress 22 includes an upper surface 112, a lower surface 114, a head end edge 116 extending between the upper and lower surfaces 112, 114, and a step vertical surface 118 dividing portions of the lower surface 114. The step vertical surface 118 permits the mattress 22 to fit in a step articulating deck 20 (stepped portion of the deck not shown).

The receptacle 94 of bed coupler 32 includes five walls 120, 122, 124, 126, which define the outer limits of the receptacle 94 and cover a section of the head portion 24 of the mattress 22. The first wall is an upper wall 120 which abuts the upper surface 112 of the mattress 22. The second and third walls are side walls 122, which abut sides of the mattress 22. The fourth wall is an end wall 124 which abuts the head end edge 116 of mattress 22. The fifth wall is a lower wall 126 which abuts the lower surface 118 of the mattress 22. These five walls 120, 122, 124, 126 surround a section of the head portion 24 of the mattress 22 to couple the x-ray apparatus 12 to bed 10. In the illustrated embodiment, the receptacle 94 is integral with lower layer 52 of first receptacle 36 of holder 34 as shown in FIG. 3. In alternative embodiments, the receptacle may be a separate component coupled to the holder. In alternative embodiments, the receptacle may include an additional component to provide a more positive interaction or coupling between the bed coupler and mattress. For example, in alternative embodiments, elastic material may be coupled to the walls or interactive latches may be coupled to one or more of the walls and one or more of the mattress or bed.

The straps 96, 98 are coupled to respective sides 42, 44 of holder 34 adjacent to second end 48 of holder 34 as shown in FIGS. 1 and 2. In the illustrated embodiment, the bed 10 includes handles 128 on each side of the bed 10 and the straps 96, 98 are adapted to attach to the handles 128. In preferred embodiments, each of the straps 96, 98 includes a fastener 130 that is used to coupled straps 96, 98 to bed 10. In the illustrated embodiment, the fastener 130 is a hook 132 and loop 134 type fastener, although any suitable fastener such as snaps, ties, etc., can be used. In alternative embodiments, the straps 96, 98 may also be secured to other structure of the bed or components coupled to the bed.

The straps 96, 98 and handles 128 comprise interactive latches with one component being part of the bed 10 and a mating part being part of the x-ray apparatus 12. In alternative embodiments, other types of interactive latches such as detent/notch mechanisms may be used. In preferred embodiments, the interactive latches are adjustable so that the latches can be used regardless of the elevation of the head portion 24 of the mattress 22.

In the illustrated embodiment, bed coupler 32 and first receptacle 36 of holder 34 are made from a water impermeable material such as Penn-nyla Po-88 or Penn-nyla Po-238. In preferred embodiments, the upper and lower 50, 52 of first receptacle 36 and straps 96, 98 are coupled by ultrasonic welding. However, in alternative embodiments, these components may be coupled by coupled by heat welding, radio frequency ("RF") welding, stitching, or any other conventional method.

The second receptacle 38 of holder 34 is made from a material that has a lower coefficient of friction compared to the water impermeable material of the first receptacle 36. In the preferred embodiment, the second receptacle 38 is made from a denier rip stop nylon. The surface of the rip stop nylon is smooth and substantially slicker than water impermeable material to permit the second receptacle 38 to slide easily into the cavity 62 of the first receptacle 36.

The x-ray apparatus 12 is coupled to bed 10 by lifting head portion 24 of mattress 22, as shown in FIG. 1, and sliding receptacle 94 of bed coupler 32 over head portion 24 of mattress 22. The first receptacle 36 of holder 34 is then positioned over mattress 22, as shown in FIG. 2, and straps 96, 98 of bed coupler 32 are coupled to bed 10.

To use the x-ray cassette apparatus 12 to assist in taking an x-ray of a patient positioned on bed 10, x-ray cassette 40 is inserted into second receptacle 38 of holder 34 and the second receptacle 38 and x-ray cassette 40 are slid into first receptacle 36 of holder 34 as shown in FIG. 3. Once the x-ray cassette 40 is placed in holder 34 in the desired position, the cassette 40 may be used to obtain the desired x-ray image.

Figure 4:
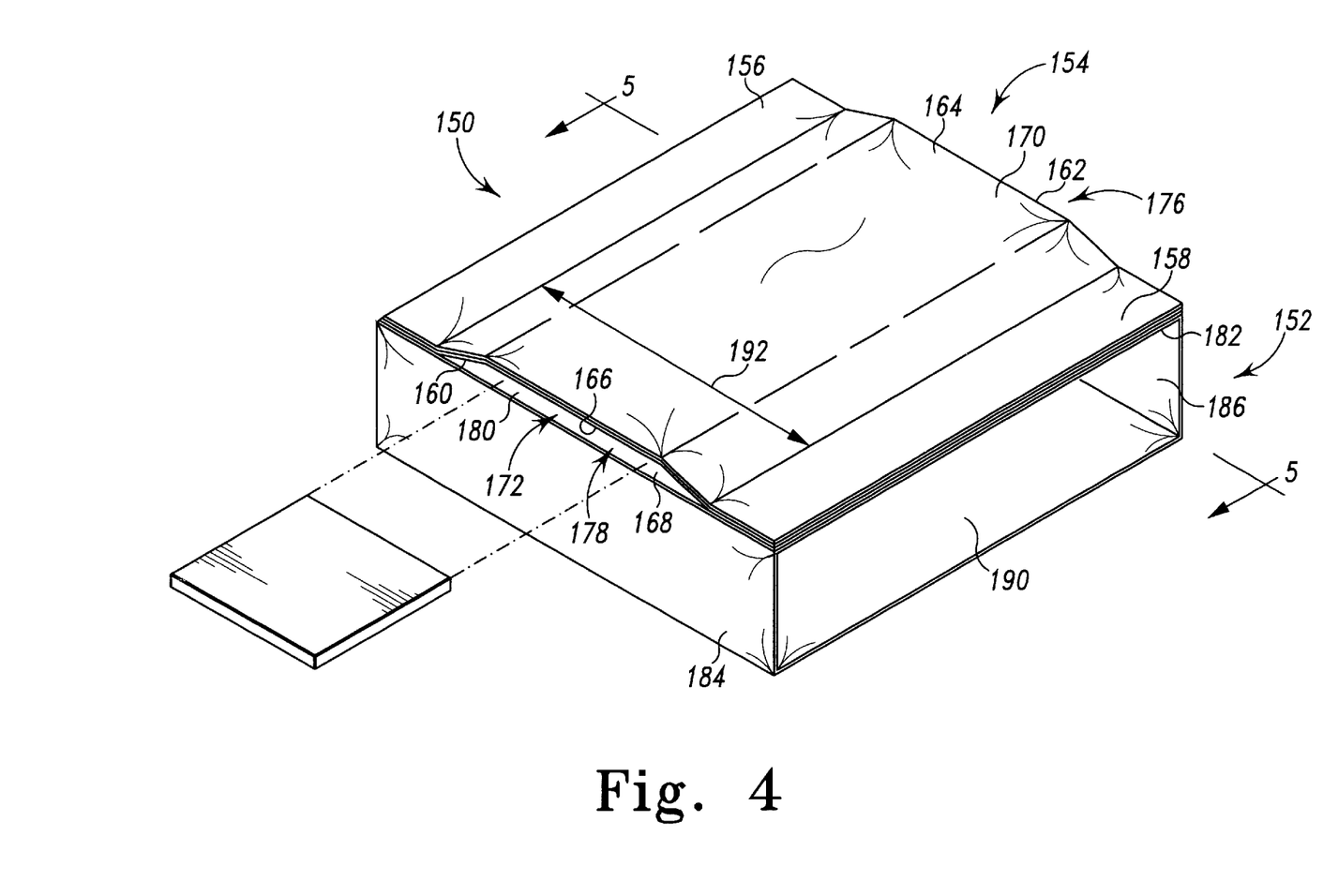
FIG. 4 is a perspective view of an alternative embodiment of an x-ray apparatus.
Figure 5:
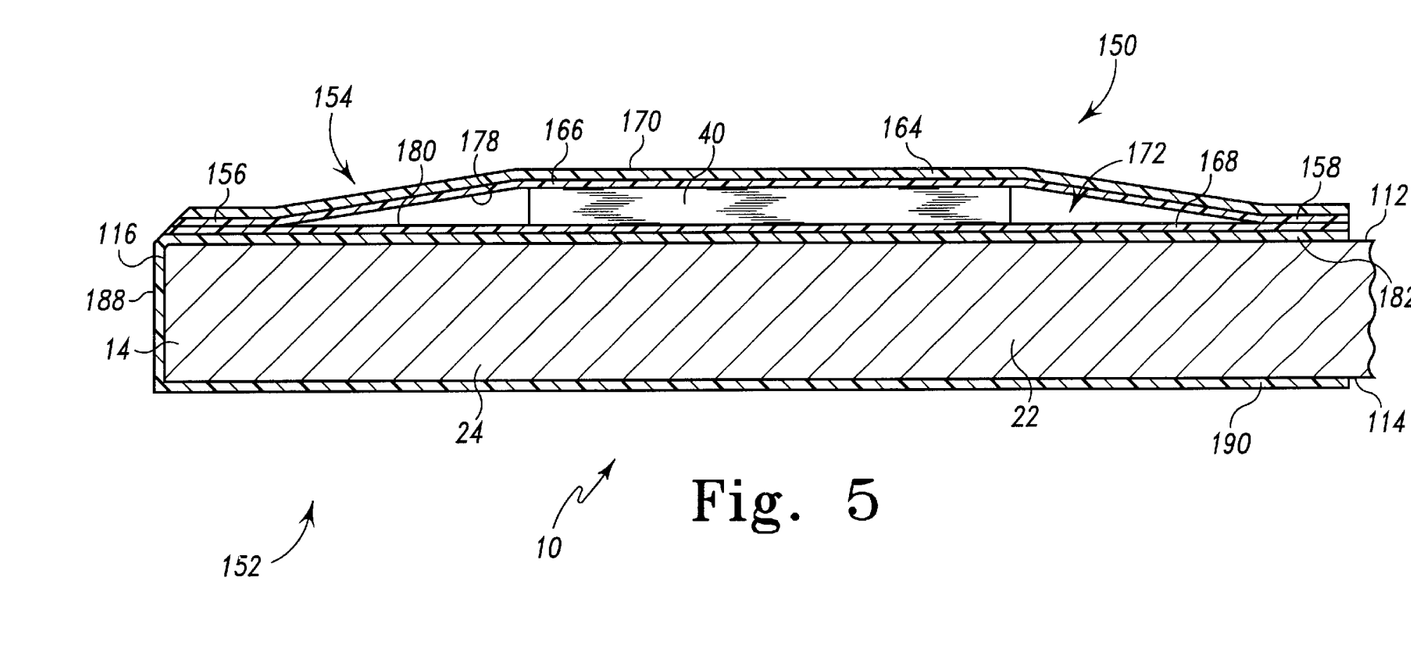
FIG. 5 is a sectional view, similar to FIG. 3, taken along line 5—5 of FIG. 4 showing the x-ray cassette positioned in the x-ray holder.

A second embodiment of the x-ray apparatus 150 is shown in FIGS. 4 and 5. X-ray apparatus 150 includes a bed coupler 152 and a holder 154. The holder 154 is a receptacle that includes first and second ends 156, 158, first and second sides 160, 162 extending between the ends 156, 158, first and second upper layers 164, 166, and a lower layer 168. The layers 164, 166, 168 are coupled to each other and the bed coupler 152 at the first and second ends 156, 158 and portionsx of the first and second sides 160, 162 adjacent to the ends 156, 158. The first upper layer 164 includes an upper surface 170 on which a patient in the bed 10 lies.

The second upper layer 166 and lower layer 168 define a cavity 172 and openings 174, 176 that are in communication with the cavity 172. Openings 174, 176 are defined on first and second sides 160, 162 by the portions of second upper layer 166 and lower layer 168 which are not coupled to each other. The second upper layer 166 includes a lower surface 178 facing into cavity 172 and the lower layer 168 includes an upper surface 180 which similarly faces into cavity 172. The lower layer 168 also includes a lower surface 178 which faces toward bed coupler 152.

The bed coupler 152 includes five walls 182, 184, 186, 188, 190 which define the outer limits of the bed coupler 152 and cover a section of the head portion 24 of the mattress 22. The first wall is an upper wall 182 which abuts the upper surface 112 of the mattress 22. The second and third walls are side walls 184, 186 which abut sides of the mattress 22. The fourth wall is an end wall 188 which abuts the head end edge 116 of mattress 22. The fifth wall is a lower wall 190 which abuts the lower surface 118 of the mattress 22. These five walls 182, 184, 186, 188, 190 surround a section of the head portion 24 of the mattress 22 to couple the x-ray apparatus 150 to bed 10.

The bed coupler 152 and first upper layer 164 of holder 154 are formed from an appropriate water impermeable material such as Penn-nyla. To facilitate insertion of an x-ray cassette 40 into holder 154, second layer 166 and lower layer 168 of holdler 154 are made of a material having a lower coefficient of friction compared to the water impermeable material used to make bed coupler 152 and first upper layer 164 of holder 154. In preferred embodiments, the second upper layer 166 and lower layer 168 of holder 154 are made of rip stop nylon.

To couple the x-ray apparatus 150 to bed 10, the bed coupler 152 is slid over head portion 24 of mattress 22 to the position shown in FIG. 5. The x-ray cassette 40 may then be slid through one of the openings 174, 176 in the sides 160, 162 of holder 154 and positioned in holder to obtain 154 to obtain the desired x-ray image. To facilitate placement of x-ray cassette 40 relative to a patient positioned on bed 10 to obtain a desired x-ray image, openings 174, 176 along sides 160, 162 of the holder 154 have a length 192 that is substantially greater than the length 80 of cassette 40.

The materials used to make the x-ray apparatus 12, 150 are pliable materials which do not interfere with the interaction or interface pressures between the patient and the mattress 22. While both embodiments of x-ray apparatus 12, 150 have been described as being fabricated from Penn-nyla and rip stop nylon, it is to be understood that x-ray apparatus fabricated from other suitable materials are within the teaching of this disclosure.

In alternative embodiments, the relatively low friction layers 166, 168 of x-ray apparatus 150 and the relatively low friction second receptacle 38 of x-ray apparatus 12 may be used with either of the bed couplers 32, 152 of x-ray apparatus 12, 150. In other alternative embodiments, the x-ray apparatus 12, 150 may be rotated 180° and coupled to the bed 10 so that the x-ray cassette 40 is positioned between the mattress 22 and the support deck 20 of frame 18. In addition, the x-ray apparatus 12, 150 may be placed at any desired location relative to the mattress such as on the foot portion 26 or central portion 28.

Although the invention has been described in detail with reference to preferred embodiments, variations and modifications exist within the scope and spirit of the invention as described and defined in the following claims.

What is claimed is:

1. An apparatus for coupling a rigid item to a patient support, the apparatus comprising
   a patient support coupler adapted to couple to the patient support, the patient support coupler being made of a material having a first coefficient of friction, and
   a holder coupled to the patient support coupler, the holder being configured to receive and hold the rigid item, the holder including a surface having second coefficient of friction that is less than the first coefficient of friction, and the surface of the holder being adapted to abut the rigid item.

2. The apparatus of claim 1, wherein the holder includes a first material having a first material coefficient of friction and a second material including a surface having a second material coefficient of friction which is less than the first material coefficient of friction.

3. The apparatus of claim 2, wherein the first and second materials are coupled to each other and the second material defines a cavity which receives the rigid item.

4. The apparatus of claim 1, wherein the holder includes first and second receptacles, the first receptacle is coupled to the patient support and defines a cavity adapted to receive the second receptacle, and the second receptacle defines a cavity adapted to receive the rigid item.

5. The apparatus of claim 4, wherein the first receptacle includes a first receptacle coefficient of friction and the second receptacle includes a surface having second receptacle coefficient of friction that is less than the first receptacle coefficient of friction.

6. The apparatus of claim 1, wherein the patient support coupler includes a receptacle adapted to cover a portion of a support surface of the patient support.

7. The apparatus of claim 1, wherein the patient support coupler and patient support include interactive latches.

8. The apparatus of claim 7, wherein the interactive latch of the patient support coupler includes a strap adapted to couple to the patient support.

9. The apparatus of claim 7, wherein the patient support coupler further includes a receptacle adapted to couple to an end of a support surface of the patient support.

10. The apparatus of claim 9, wherein the receptacle is spaced apart from the interactive latch of the patient support coupler.

11. The apparatus of claim 10, wherein the holder includes spaced-apart first and second ends, the receptacle is coupled to the first end of the holder, and the interactive latch of the patient support coupler is coupled to the second end of the holder.

12. The apparatus of claim 1, wherein the patient support coupler includes first and second couplers that are spaced-apart from each other.

13. The apparatus of claim 1, wherein the holder includes a first opening to receive an x-ray cassette.

14. The apparatus of claim 13, wherein the holder includes a second opening to receive an x-ray cassette.

15. The apparatus of claim 14, wherein the holder includes first and second sides and first and second ends which extend between the first and second sides, the first opening is on the first side of the holder, and the second opening is on the second side of the holder.

16. The apparatus of claim 1, wherein the patient support coupler is made of a pliable material.

17. The apparatus of claim 1, wherein the holder is made of a pliable material.

18. The apparatus of claim 17, wherein the patient support coupler is made of a pliable material.

19. The apparatus of claim 1, wherein the holder is positioned on an upper surface of a mattress of a patient support.

20. An apparatus for coupling a rigid item to a patient support, the apparatus comprising
    a patient support coupler adapted to couple to the patient support, and
    a holder coupled to the patient support coupler, the holder being configured to receive and hold the rigid item, and the holder being made of a pliable material.

21. An apparatus for coupling a rigid item to a patient support, the apparatus comprising
    a patient support coupler adapted to couple to the patient support,
    a holder coupled to the patient support coupler, the holder being configured to receive and hold the rigid item, and the holder being made of a pliable material; and
    wherein the holder includes a first material having a first material coefficient of friction and a second material including a surface having a second material coefficient of friction which is less than the first material coefficient of friction.

22. The apparatus of claim 21, wherein the first and second materials are coupled to each other and the second material defines a cavity which receives the rigid item.

23. The apparatus of claim 20, wherein the holder includes first and second receptacles, the first receptacle is coupled to the patient support and defines a cavity adapted to receive the second receptacle, and the second receptacle defines a cavity adapted to receive the rigid item.

24. The apparatus of claim 23, wherein the first receptacle includes a first receptacle coefficient of friction and the second receptacle includes a surface having second receptacle coefficient of friction that is less than the first receptacle coefficient of friction.

25. The apparatus of claim 20, wherein the patient support coupler includes a receptacle adapted to cover a portion of a support surface of the patient support.

26. The apparatus of claim 20, wherein the patient support coupler and patient support include interactive latches.

27. The apparatus of claim 26, wherein the interactive latch of the patient support coupler includes a strap adapted to couple to the patient support.

28. The apparatus of claim 26, wherein the patient support coupler further includes a receptacle adapted to couple to an end of a support surface of the patient support.

29. The apparatus of claim 28, wherein the receptacle is spaced apart from the interactive latch of the patient support coupler.

30. The apparatus of claim 29, wherein the holder includes spaced-apart first and second ends, the receptacle is coupled to the first end of the holder, and the interactive latch of the patient support coupler is coupled to the second end of the holder.

31. The apparatus of claim 20, wherein the patient support coupler includes first and second couplers that are spaced-apart from each other.

32. The apparatus of claim 20, wherein the holder includes a first opening to receive an x-ray cassette.

33. The apparatus of claim 32, wherein the holder includes a second opening to receive an x-ray cassette.

34. The apparatus of claim 33, wherein the holder includes first and second sides and first and second ends which extend between the first and second sides, the first opening is on the first side of the holder, and the second opening is on the second side of the holder.

35. The apparatus of claim 20, wherein the patient support coupler is made of a pliable material.

36. The apparatus of claim 20, wherein the holder is positioned on an upper surface of a patient support.

37. An apparatus for coupling a rigid item to a patient support having a support surface, the apparatus comprising
 a patient support coupler adapted to couple to the patient support, and
 a holder coupled to the patient support coupler, the holder being configured to receive and hold the rigid item, and the holder being positioned on an upper surface of the support surface.

38. An apparatus for coupling a rigid item to a patient support having a support surface, the apparatus comprising
 a patient support coupler adapted to couple to the patient support,
 a holder coupled to the patient support coupler, the holder being configured to receive and hold the rigid item, and the holder being positioned on an upper surface of the support surface; and
 wherein the holder includes a first material having a first material coefficient of friction and a second material including a surface having a second material coefficient of friction which is less than the first material coefficient of friction.

39. The apparatus of claim 38, wherein the first and second materials are coupled to each other and the second material defines a cavity which receives the rigid item.

40. The apparatus of claim 37, wherein the holder includes first and second receptacles, the first receptacle is coupled to the patient support and defines a cavity adapted to receive the second receptacle, and the second receptacle defines a cavity adapted to receive the rigid item.

41. The apparatus of claim 40, wherein the first receptacle includes a first receptacle coefficient of friction and the second receptacle includes a surface having second receptacle coefficient of friction that is less than the first receptacle coefficient of friction.

42. The apparatus of claim 37, wherein the patient support coupler includes a receptacle adapted to cover a portion of a support surface of the patient support.

43. The apparatus of claim 37, wherein the patient support coupler and patient support include interactive latches.

44. The apparatus of claim 43, wherein the interactive latch of the patient support coupler includes a strap adapted to couple to the patient support.

45. The apparatus of claim 43, wherein the patient support coupler further includes a receptacle adapted to couple to an end of a support surface of the patient support.

46. The apparatus of claim 45, wherein the receptacle is spaced-apart from the interactive latch of the patient support coupler.

47. The apparatus of claim 46, wherein the holder includes spaced-apart first and second ends, the receptacle is coupled to the first end of the holder, and the interactive latch of the patient support coupler is coupled to the second end of the holder.

48. The apparatus of claim 37, wherein the patient support coupler includes first and second couplers that are spaced apart from each other.

49. The apparatus of claim 37, wherein the holder includes a first opening to receive an x-ray cassette.

50. The apparatus of claim 49, wherein the holder includes a second opening to receive an x-ray cassette.

51. The apparatus of claim 50, wherein the holder includes first and second sides and first and second ends which extend between the first and second sides, the first opening is on the first side of the holder, and the second opening is on the second side of the holder.

52. The apparatus of claim 37, wherein the patient support coupler is made of a pliable material.

53. The apparatus of claim 37, wherein the holder is made of a pliable material.

54. The apparatus of claim 53, wherein the patient support coupler is made of a pliable material.

55. An apparatus for coupling a rigid item to a patient support having a support surface, the apparatus comprising
 a patient support coupler adapted to couple to the patient support, the patient support coupler including a receptacle configured to receive and cover an end portion of the support surface of the patient support; and
 a holder coupled to the patient support coupler, the holder being configured to receive and hold the rigid item.

56. The apparatus of claim 55, wherein the patient support coupler and the patient support include interactive latches.

57. The apparatus of claim 56, wherein the interactive latch of the patient support coupler includes a strap adapted to couple to he patient support.

58. The apparatus of claim 56, wherein the interactive latch of the patient support, coupler is spaced-apart From the receptacle.

59. The apparatus of claim 58, wherein the holder includes spaced-apart first and second ends, the receptacle is coupled to the first end of the holder, and the interactive latch of the patient support coupler is coupled to the second end of the holder.

60. The apparatus of claim 55, wherein the patient support coupler is made of a pliable material.

61. The apparatus of claim 55, wherein
 the support surface is defined by a mattress; and
 the receptacle includes an upper wall configured to abut the support surface, a pair of side walls coupled to the upper wall and configured to abut sides of the mattress, an end wall coupled to the upper wall and configured to abut a head end edge of the mattress, and a lower wall coupled to the pair of side walls and configured to abut a lower surface of the mattress.

62. An apparatus for coupling a rigid item to a patient support having a support surface, the apparatus comprising:
 a patient support coupler adapted to couple to the patient support;
 a first receptacle coupled to the patient support coupler and defining a first cavity; and a second receptacle configured to be received within the first cavity of the first receptacle, the second receptacle defining a second cavity adapted to receive the rigid item.

63. The apparatus of claim 62, wherein the first receptacle includes a surface having a first receptacle coefficient of friction and the second receptacle includes a surface having second receptacle coefficient of friction that is less than the first receptacle coefficient of friction.

64. The apparatus of claim 62, wherein the first receptacle includes first and second sides, first and second ends which extend between the first and second sides, a first opening formed in the first side, and a second opening formed in the second side.

65. The apparatus of claim 62, wherein the rigid item comprises an x-ray cassette.

66. The apparatus of claim 62, wherein the holder is made of a pliable material.

67. The apparatus of claim 66, wherein the coupler is made of a pliable material.

* * * * *